United States Patent
Daly et al.

(10) Patent No.: US 10,078,048 B2
(45) Date of Patent: Sep. 18, 2018

(54) REFRACTOMETER ASSEMBLIES, METHODS OF CALIBRATING THE SAME, AND METHODS OF DETERMINING UNKNOWN REFRACTIVE INDICES USING THE SAME

(71) Applicant: Corning Incorporated, Corning, NY (US)

(72) Inventors: Colin Brendan Daly, San Bruno, CA (US); John Phillip Ertel, Half Moon Bay, CA (US); Jeffrey Stapleton King, Menlo Park, CA (US)

(73) Assignee: CORNING INCORPORATED, Corning, NY (US)

( * ) Notice: Subject to any disclaimer, the term of this patent is extended or adjusted under 35 U.S.C. 154(b) by 0 days.

(21) Appl. No.: 15/415,283

(22) Filed: Jan. 25, 2017

(65) Prior Publication Data

US 2017/0212043 A1 Jul. 27, 2017

Related U.S. Application Data

(60) Provisional application No. 62/287,650, filed on Jan. 27, 2016.

(51) Int. Cl.
*G01N 21/41* (2006.01)
*G01N 21/27* (2006.01)

(52) U.S. Cl.
CPC ....... *G01N 21/4133* (2013.01); *G01N 21/274* (2013.01)

(58) Field of Classification Search
CPC ........ G01N 21/00; G01N 21/41; G01N 21/27; G01N 21/4133; G01N 21/274; G01J 3/00; G01J 3/40
See application file for complete search history.

(56) References Cited

U.S. PATENT DOCUMENTS 5,120,131 A 6/1992 Lukosz
5,973,774 A 10/1999 Haggett et al.
(Continued)

FOREIGN PATENT DOCUMENTS

CA 2054887 A1 7/1993
FR 2694629 A1 2/1994
(Continued)

OTHER PUBLICATIONS

Zhi-Mei Qi, Naoki Matsuda, and Jose H. Santos, "Prism-coupled multimode waveguide refractometer", Optics Letter, pp. 1-3, May 1, 2001 vol. 27, No. 9.
(Continued)

*Primary Examiner* — Jamil Ahmed
(74) *Attorney, Agent, or Firm* — Gregory V. Bean

(57) ABSTRACT

A refractometer assembly comprises a waveguide plate, a diagnostic light source, a photodetector, and a light absorption plate. The diagnostic light source and the photodetector are optically coupled to the waveguide plate such that at least a portion of light emitted from the diagnostic light source is subject to internal reflection at a diagnostic surface of the waveguide plate prior to reaching the photodetector when an analyte film of unknown refractive index $n_0$ forms an optical interface with the diagnostic surface of the waveguide plate. The light absorption plate is configured to absorb light reaching the light absorption plate without undergoing internal reflection at the diagnostic surface when the analyte film forms an optical interface with the diagnostic surface of the waveguide plate. The refractometer assembly defines an optical system where variations in the unknown refractive index $n_0$ are related to variations in a detection signal generated by the photodetector.

20 Claims, 5 Drawing Sheets

(56) References Cited

U.S. PATENT DOCUMENTS

| | | | |
|---|---|---|---|
| 6,816,248 | B2 | 11/2004 | Sharma et al. |
| 7,619,725 | B1 | 11/2009 | Seaver |
| 2009/0041405 | A1 | 2/2009 | Dai et al. |
| 2009/0279074 | A1* | 11/2009 | Seaver ............... G01N 21/4133 356/73 |

FOREIGN PATENT DOCUMENTS

| | | |
|---|---|---|
| JP | 2000028526 A | 1/2000 |
| JP | 2009092569 A | 4/2009 |
| JP | 2010010384 A | 1/2010 |

OTHER PUBLICATIONS

Archenault et. al, "A simple intrinsic optical fibre refractometer" Sensors and Actuators B, V5, I1-4, 1991, p. 173-179.

Banerjee et. al, "Fiber optic sensing of liquid refractive index" Sensors and Actuators B, V 123, I1, 2007, p. 594-605.

Maisenholder et.al, "A GaAs/AlGaAs-based refractometer platform for integrated optical sensing applications" Sensors and Actuators B, V39, I1-3, 1997, p. 324-329.

Gao et. al. "Design and fabrication of SMS fiber refractometer for liquid" Sensors and Actuators A, v 179, 2012, p. 5-9.

Kauppinen et. al, "A compact refractometric sensor based on grated silicon photonic wires" Sensors and Actuators B, vol. 139, I1 2009, p. 194-198.

Kishii, "Critical ray-like propagation modes along graded-index planar optical waveguides" Optics and Laser Tech. V 14, I2, 1982. p. 75-80.

Lukosz et. al, "Integrated optical output grating coupler as refractometer and (bio-)chemical sensor" Sensors and Actuators B, vol. 11, issue 1-3, 1993, p. 461-465.

Nath et. al, "All-fiber optic sensor for measurement of liquid refractive index" Sensors and Actuators A, V148, I1, 2008, p. 16-18.

Seow et. al, "An optofluidic refractive index sensor based on partial refraction" Sensors and Actuators B, V 147, I 2, 2010, p. 607-611.

Uria et. al, "Effect of the cathode/anode ratio and the choice of cathode catalyst on the performance of microbial fuel cell transducers for the determination of microbial activity" Sensors and Actuators B, V161, I1, 2012, p. 88-94.

Sparrow et. al, Planar waveguide hygrometer and state sensor demonstrating supercooled water recognition: Sensors and Actuators B, vol. 107, Iss 2, 2005, p. 856-860.

Wang et. al, "High-resolution liquid refractive-index sensor using reflective arrayed-waveguide grating" Optics and Laser Tech. vol. 42, Issue 8, 2010, p. 1312-1317.

Zhang et. al, "A single-element interferometer for measuring refractive index of transparent liquids" Optics Communications, V332, 2014, p. 14-17.

Zhou et. al, "Compact refractometer based on extrinsic-phase-shift fiber Bragg grating" Sensors and Actuators A, V 168, I 1, 2011, p. 46-50.

\* cited by examiner

REFRACTOMETER ASSEMBLIES, METHODS OF CALIBRATING THE SAME, AND METHODS OF DETERMINING UNKNOWN REFRACTIVE INDICES USING THE SAME

CROSS-REFERENCE TO RELATED APPLICATIONS

This application claims the benefit of priority under 35 U.S.C. § 119 of U.S. Provisional Application Ser. No. 62/287,650 filed on Jan. 27, 2016, the content of which is relied upon and incorporated herein by reference in its entirety

BACKGROUND

The present disclosure relates to refractometer assemblies. More specifically, the present disclosure introduces technology for refractometer assemblies having a waveguide plate.

BRIEF SUMMARY

According to the subject matter of the present disclosure, a refractometer assembly comprises a waveguide plate, a diagnostic light source, a photodetector, and a light absorption plate. The waveguide plate comprises a diagnostic surface configured to support an analyte film of unknown refractive index $n_0$ between the light absorption plate and the diagnostic surface of the waveguide plate. The diagnostic light source is characterized by an emission profile that is approximately Lambertian. The diagnostic light source and the photodetector are optically coupled to the waveguide plate such that at least a portion of the light emitted from the diagnostic light source is subject to internal reflection at the diagnostic surface of the waveguide plate prior to reaching the photodetector when the analyte film of unknown refractive index $n_0$ forms an optical interface with the diagnostic surface of the waveguide plate. The light absorption plate is configured to absorb light emitted from the diagnostic light source and reaching the light absorption plate without undergoing internal reflection at the diagnostic surface of the waveguide plate when the analyte film of unknown refractive index $n_0$ forms an optical interface with the diagnostic surface of the waveguide plate. The waveguide plate, the diagnostic light source, the photodetector, and the light absorption plate collectively define an optical system where variations in the unknown refractive index $n_0$ are related to variations in a detection signal generated by the photodetector.

In accordance with one embodiment of the present disclosure, a method of determining an unknown refractive index $n_0$ of an analyte film comprises emitting light from a diagnostic light source optically coupled to a waveguide plate. An analyte film of unknown refractive index $n_0$ is supported between a light absorption plate and a diagnostic surface of the waveguide plate such that the analyte film of unknown refractive index $n_0$ forms an optical interface with the diagnostic surface of the waveguide plate. The emitted light is characterized by an emission profile that is approximately Lambertian. The light absorption plate is configured to absorb light emitted from the diagnostic light source and reaching the light absorption plate without undergoing internal reflection at the diagnostic surface of the waveguide plate when the analyte film of unknown refractive index $n_0$ forms an optical interface with the diagnostic surface of the waveguide plate. The method further comprises converting a portion of emitted light that is subject to internal reflection at the diagnostic surface of the waveguide plate into a detection signal using a photodetector optically coupled to the waveguide plate wherein the unknown refractive index $n_0$ is related to the detection signal and determining the unknown refractive index $n_0$ based on the detection signal.

In accordance with another embodiment of the present disclosure, a method of calibrating a refractometer assembly comprising a waveguide plate, a diagnostic light source, and a photodetector comprises supporting a first transparent calibration layer of known refractive index $n_1$ between a calibration surface of the waveguide plate and a first absorptive calibration plate such that an optical interface is formed between the first transparent calibration layer of known refractive index $n_1$ and the calibration surface and emitting light from the diagnostic light source optically coupled to the waveguide plate. The emitted light is characterized by an emission profile that is approximately Lambertian. The first absorptive calibration plate is configured to absorb light emitted from the diagnostic light source and reaching the first absorptive calibration plate without undergoing internal reflection at the calibration surface of the waveguide plate when first transparent calibration layer of known refractive index $n_1$ forms an optical interface with the calibration surface of the waveguide plate. The method further comprises converting a portion of emitted light that is subject to internal reflection at the calibration surface of the waveguide plate into a first calibration detection signal using the photodetector optically coupled to the waveguide plate, supporting a second transparent calibration layer of known refractive index $n_2$ between a diagnostic surface of the waveguide plate and a second absorptive calibration plate such that an optical interface is formed between the second transparent calibration layer of known refractive index $n_2$ and the diagnostic surface, wherein the diagnostic surface is opposite the calibration surface, and emitting light from the diagnostic light source optically coupled to the waveguide plate. The emitted light is characterized by an emission profile that is approximately Lambertian. The second absorptive calibration plate is configured to absorb light emitted from the diagnostic light source and reaching the second absorptive calibration plate without undergoing internal reflection at the diagnostic surface of the waveguide plate when the second transparent calibration layer of known refractive index $n_2$ forms an optical interface with the diagnostic surface of the waveguide plate. The method further comprises converting a portion of emitted light that is subject to internal reflection at the diagnostic surface of the waveguide plate into a second calibration detection signal using the photodetector optically coupled to the waveguide plate and determining a relationship between the known refractive index $n_1$, the known refractive index $n_2$, the first calibration detection signal, and the second calibration detection signal.

Although the concepts of the present disclosure are described herein with primary reference to some specific refractometer assembly configurations, it is contemplated that the concepts will enjoy applicability to refractometer assemblies having any configuration.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which.

DETAILED DESCRIPTION

Figure 1:
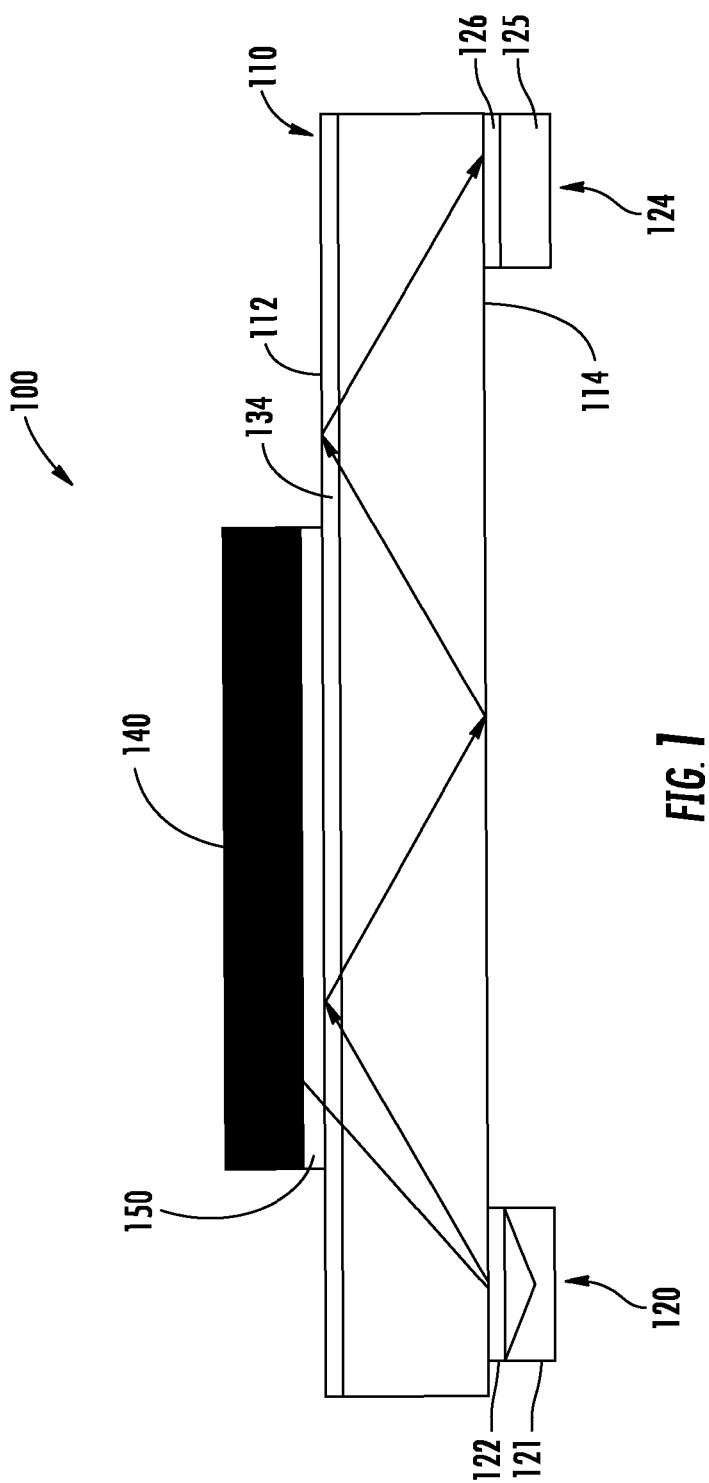
FIG. 1 is a schematic illustration of a refractometer assembly having a diagnostic light source, an absorption plate, and a photodetector optically coupled to a waveguide plate, according to one or more embodiments shown and described herein.

FIG. 1 is a schematic illustration of a refractometer assembly 100. The refractometer assembly 100 comprises a waveguide plate 110, a diagnostic light source 120, a photodetector 124, and a light absorption plate 140. The waveguide plate 110 comprises a diagnostic surface 112 opposite a calibration surface 114. The waveguide plate 110 is structurally and compositionally configured to facilitate partial and/or total internal reflection at both the diagnostic surface 112 and the calibration surface 114 when light is emitted into the waveguide plate 110, for example, using the diagnostic light source 120. The waveguide plate 110 may comprise a glass plate, for example Corning® Gorilla® Glass (such as, Corning's code 2318, 2319, or 2320 glass), Corning® EAGLE XG®, Corning® IOX®, Corning® Lotus®, or the like, available from Corning Incorporated, Corning N.Y., an acrylic glass plate, a plastic plate, or any glass or non-glass composition suitable for guiding light or otherwise functioning as a waveguide plate. The diagnostic light source 120 and the photodetector 124 are each optically coupled to the waveguide plate 110 such that an optical pathway extends between the diagnostic light source 120 and the photodetector 124.

The diagnostic light source 120 is optically coupled to the waveguide plate 110 and may comprise any light source that is characterized by an emission profile that is approximately Lambertian. Although the extent to which the emission profiles according to the present disclosure will vary according to the specific needs of those practicing the concepts disclosed herein, it is contemplated that suitable emission profiles may be approximately Lambertian over a solid angle (e.g., a steradian) that is at least large enough to span a range over which total internal reflection of diagnostic light within the waveguide plate 110 is supported, for example, a solid angle corresponding to the mode structure of the waveguide plate 110 and/or the critical angle of the waveguide plate 110. The solid angle that is at least large enough to span a range over which total internal reflection of diagnostic light within the waveguide plate 110 is supported may depend on the material of the waveguide plate 110 and a desired index of refraction measurement range corresponding to an analyte film 150 of unknown refractive index $n_0$ that may be supported by the waveguide plate 110.

Although a variety of conventional and yet-to-be developed light sources may be utilized within the scope of the present disclosure, in particular embodiments, the diagnostic light source 120 may comprise a light emitting portion 121, for example, a light emitting diode (LED) or other light emitting component and a Lambertian scattering layer 122 optically coupling the light emitting portion 121 to the waveguide plate 110. The Lambertian scattering layer 122 may be positioned between the light emitting portion 121 and one of the diagnostic surface 112 or a calibration surface 114 and may adhesively couple the light emitting portion 121 to one of the diagnostic surface 112 or the calibration surface 114. While the Lambertian scattering layer 122 may both optically and adhesively couple the light emitting portion 121 of the diagnostic light source 120 with one of the diagnostic surface 112 or the calibration surface 114 of the waveguide plate 110, it should be understood that the Lambertian scattering layer 122 may be spaced apart from one or both of the diagnostic light source 120 and the waveguide plate 110 while optically coupling the diagnostic light source 120 to the waveguide plate 110. Further, the Lambertian scattering layer 122 may comprise a $TiO_2$ loaded epoxy, a fluoropolymer, or the like and may be structurally and compositionally configured such that the light output by the light emitting portion 121 that traverses the Lambertian scattering layer 122 may enter the waveguide plate 110 with an emission profile that is approximately Lambertian.

Referring still to FIG. 1, the photodetector 124 is optically coupled to the waveguide plate 110. Although a variety of conventional and yet-to-be developed photodetectors may be utilized within the scope of the present disclosure, in particular embodiments, the photodetector 124 may comprise a detecting portion 125 optically coupled to a Lambertian cosine correcting layer 126. The detecting portion 125 may comprise any light detecting component such as a photodiode, a charged-coupled device, a photoresistor, a photomultiplier, a phototube, a phototransistor, or the like. Further, the Lambertian cosine correcting layer 126 may optically couple the detecting portion 125 of the photodetector 124 to the waveguide plate 110. The Lambertian cosine correcting layer 126 may be positioned between the detecting portion 125 of the photodetector 124 and one of the diagnostic surface 112 or a calibration surface 114 and may adhesively couple the detecting portion 125 to one of the diagnostic surface 112 or a calibration surface 114. Further, while the Lambertian cosine correcting layer 126 may both optically and adhesively couple the detecting portion 125 of the photodetector 124 with one of the diagnostic surface 112 or the calibration surface 114 of the waveguide plate 110, it should be understood that the Lambertian cosine correcting layer 126 may be spaced apart from one or both of the photodetector 124 and the waveguide plate 110 while optically coupling the photodetector 124 to the waveguide plate 110.

The Lambertian cosine correcting layer 126 may comprise a $TiO_2$ loaded epoxy, a fluoropolymer, or the like and may be structurally and compositionally configured such that the luminous intensity of light that traverses the Lambertian cosine correcting layer 126 and is detected by the detecting portion 125 of the photodetector 124 follows Lambert's cosine law such that the luminous intensity of the light detected by the photodetector 124 is proportional to the cosine of the incident angle of the light detected by the photodetector 124 relative to the projection extending normal to the diagnostic surface 112 or the calibration surface 114 of the waveguide plate 110.

Referring still to FIG. 1, the diagnostic surface 112 of the waveguide plate 110 is configured to support the analyte film 150 of unknown refractive index $n_0$ between the light absorption plate 140 and the diagnostic surface 112 of the waveguide plate 110. The analyte film 150 may comprise any substance having an unknown refractive index $n_0$, for example, a liquid or a solid. Further, the diagnostic light source 120 and the photodetector 124 are each optically coupled to the waveguide plate 110 such that at least a portion of the light emitted from the diagnostic light source 120 is subject to internal reflection at the diagnostic surface 112 of the waveguide plate 110 prior to reaching the photodetector 124, for example, when the analyte film 150 of unknown refractive index $n_0$ forms an optical interface with the diagnostic surface 112 of the waveguide plate 110.

The light absorption plate 140 may comprise an opaque material, for example, an opaque glass, an opaque acrylic, an opaque plastic, or the like, that is structurally and compositionally configured to absorb light that irradiates the light absorption plate 140. For example, the light absorption plate 140 may comprise black glass, such as black Corning® code 2320 Gorilla® Glass, carbon black-loaded polydimethylsiloxane, or the like. The light absorption plate 140 is configured to absorb light emitted from the diagnostic light source 120 that reaches the light absorption plate 140 without undergoing internal reflection at the diagnostic surface 112 of the waveguide plate 110 when the analyte film 150 of unknown refractive index $n_0$ forms an optical interface with the diagnostic surface 112 of the waveguide plate 110. For example, a portion of light may leak from the waveguide plate 110 due to the difference in the refractive index of the waveguide plate 110 and the analyte film 150 of unknown refractive index $n_0$ and may be absorbed by the light absorption plate 140. Further, the light absorption plate 140 may inhibit light emitted from the diagnostic light source 120 that reaches the light absorption plate 140 from reentering the waveguide plate 110.

In operation, the waveguide plate 110, the diagnostic light source 120, the photodetector 124, and the light absorption plate 140 collectively define an optical system where variations in the unknown refractive index $n_0$ of the analyte film 150 are related to variations in a detection signal generated by the photodetector 124. For example, the variations in the unknown refractive index $n_0$ of the analyte film 150 may be linearly related to the variations in the detection signal generated by the photodetector 124. The detection signal may comprise a voltage signal, a current signal, or the like.

Further, the detection signal is related to the luminous intensity of the portion of light received by the photodetector 124, for example, linearly. When the light emitted by the diagnostic light source 120 and the light received and detected by the photodetector 124 are Lambertian, the luminous intensity detected by the photodetector 124 is proportional to the cosine of the incident angle of light detected by the photodetector 124 relative to the projection extending normal to the diagnostic surface 112 or the calibration surface 114 of the waveguide plate 110. The incident angle of light detected by the photodetector 124 may comprise the critical angle of an optical interface formed between the waveguide plate 110 and a material, such as the analyte film 150.

Further, the critical angle is mathematically related to the refractive index of both the waveguide plate 110 and the material forming an optical interface with the waveguide plate, for example, the analyte film 150. The critical angle may be mathematically described as $\theta_c = \sin^{-1}(n_w/n_0)$ where $\theta_c$ is the incident angle of light received by the photodetector (e.g., the critical angle), $n_w$ is the refractive index of the waveguide plate 110, and $n_0$ is the unknown refractive index of the analyte film 150. Moreover, because the diagnostic light source 120 and the photodetector 124 are Lambertian, the detection signal may vary linearly with the cosine of the critical angle thus varying linearly with the unknown refractive index $n_0$ of the analyte film 150.

Referring still to FIG. 1, a method of determining the unknown refractive index $n_0$ of an analyte film 150 may comprise emitting light characterized by an emission profile that is approximately Lambertian from the diagnostic light source 120 optically coupled to the waveguide plate 110 when the analyte film 150 of unknown refractive index $n_0$ is supported between the light absorption plate 140 and the diagnostic surface 112 of the waveguide plate 110 such that the analyte film 150 of unknown refractive index $n_0$ forms an optical interface with the diagnostic surface 112 of the waveguide plate 110. After light is emitted by the diagnostic light source 120, a portion of the light may reach the light absorption plate 140 without undergoing internal reflection at the diagnostic surface 112 of the waveguide plate 110. For example, the light may traverse the optical interface between the diagnostic surface 112 and the analyte film 150, transverse the analyte film 150, and enter the light absorption plate 140, which absorbs the portion of emitted light such that it may not reenter the waveguide plate 110.

Figure 2A:
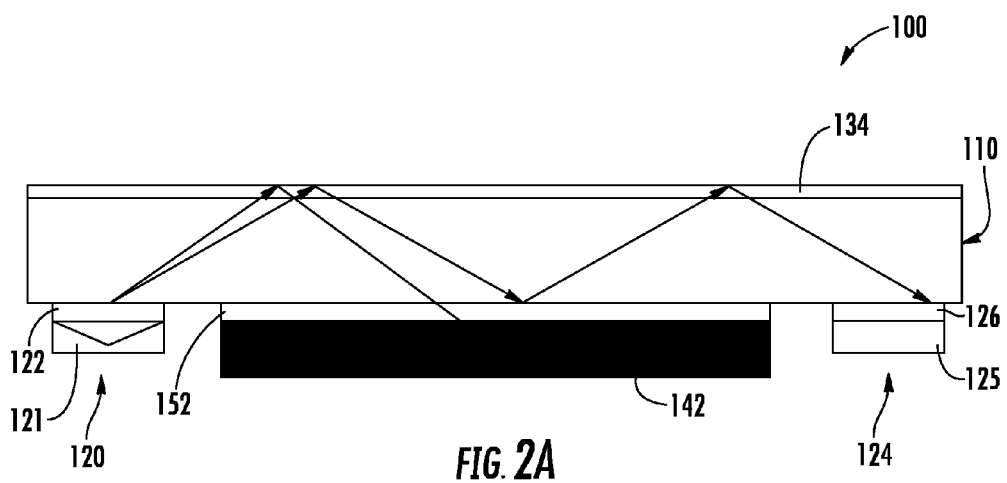
FIG. 2A is a schematic illustration of a refractometer assembly having a diagnostic light source, a first absorptive calibration layer, and a photodetector optically coupled to a waveguide plate, according to one or more embodiments shown and described herein.
Figure 2B:
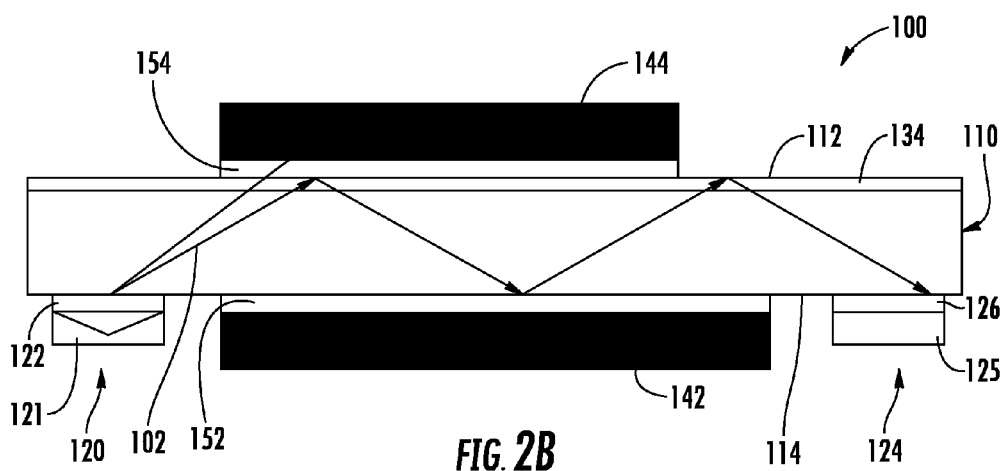
FIG. 2B is a schematic illustration of the refractometer assembly of FIG. 2A further including a second absorptive calibration layer optically coupled to the waveguide plate, according to one or more embodiments shown and described herein.

Next, a portion of the emitted light that is subject to internal reflection at the diagnostic surface 112 may traverse the waveguide plate 110 between the diagnostic light source 120 and the photodetector 124 such that the photodetector 124 receives the internally reflected portion of emitted light. Further, some of the emitted light may be subject to internal reflection at both the diagnostic surface 112 and the calibration surface 114. Once the photodetector 124 receives the portion of emitted light that is subject to internal reflection, the photodetector 124 may convert the portion of the emitted light that is subject to internal reflection at the diagnostic surface 112 of the waveguide plate 110 into a detection signal using the photodetector 124. Next, the photodetector 124, a user, an electronics control system 184 (FIG. 5), or another processing unit may determine the unknown refractive index $n_0$ based on the detection signal. The relationship between the measured detection signal and the critical angle may be determined using a calibration method, described below (FIGS. 2A and 2B). Further, while the measurement method described above comprises a number of steps it should be understood that additional steps may be contemplated. Moreover, while the steps of the measurement method are described in a particular order, other orders are contemplated.

Referring now to FIGS. 2A and 2B, a method of calibrating the refractometer assembly 100 is schematically depicted. As depicted in FIG. 2A, the method of calibrating the refractometer assembly 100 may first comprise supporting a first transparent calibration layer 152 of known refractive index $n_1$ between the calibration surface 114 of the waveguide plate 110 and a first absorptive calibration plate 142 such that an optical interface is formed between the first transparent calibration layer 152 of known refractive index $n_1$ and the calibration surface 114. The method may further comprise emitting light characterized by an emission profile that is approximately Lambertian using the diagnostic light source 120 optically coupled to the waveguide plate 110 and absorbing a portion of the emitted light that reaches the first absorptive calibration plate 142 without undergoing internal reflection at the calibration surface 114 of the waveguide plate 110. For example, a portion of light may leak from the waveguide plate 110 due to the difference in the refractive index of the waveguide plate 110 and the first transparent calibration layer 152 and may be absorbed by the first absorptive calibration plate 142.

Next, a portion of emitted light that is subject to internal reflection at the calibration surface 114 may be received by the photodetector 124 that is optically coupled to the waveguide plate 110. The photodetector 124 may convert the portion of emitted light that is subject to internal reflection at the calibration surface 114 of the waveguide plate 110 into a first calibration detection signal, for example, a voltage signal, a current signal, or the like, which is related to the luminous intensity of the portion of light received by the photodetector 124 as described above with respect to the detection signal. Alternatively, the method may comprise supporting the first transparent calibration layer 152 of known refractive index $n_1$ between the diagnostic surface 112 of the waveguide plate 110 and the first absorptive calibration plate 142 such that an optical interface is formed between the first transparent calibration layer 152 of known refractive index $n_1$ and the diagnostic surface 112 and performing the method steps described above with respect to the diagnostic surface 112 instead of the calibration surface 114.

Referring now to FIG. 2B, the method of calibrating the refractometer assembly 100 further comprises supporting a second transparent calibration layer 154 of known refractive index $n_2$ between the diagnostic surface 112 of the waveguide plate 110 and a second absorptive calibration plate 144 such that an optical interface is formed between the second transparent calibration layer 154 of known refractive index $n_2$ and the diagnostic surface 112. The known refractive index $n_2$ of the second transparent calibration layer 154 is different than the known refractive index $n_1$ of the first transparent calibration layer 152 such that two calibration detection signals may be measured and a relationship between luminous intensity received by the photodetector 124 and the refractive index of material optically coupled to the waveguide plate 110 may be determined.

Next, the method comprises emitting light characterized by an emission profile that is approximately Lambertian using the diagnostic light source 120 and absorbing a portion of the emitted light that reaches the second absorptive calibration plate 144 without undergoing internal reflection at the diagnostic surface 112 of the waveguide plate 110 with the second absorptive calibration plate 144. For example, a portion of light may leak from the waveguide plate 110 due to the difference in the refractive index of the waveguide plate 110 and the second transparent calibration layer 154 and may be absorbed by the second absorptive calibration plate 144. A portion of emitted light that is subject to internal reflection at the diagnostic surface 112 may be received by the photodetector 124 that is optically coupled to the waveguide plate 110. The photodetector 124 may convert the portion of emitted light that is subject to internal reflection at the diagnostic surface 112 of the waveguide plate 110 into a second calibration detection signal, for example, a voltage signal, a current signal, or the like, which is related to the luminous intensity of the portion of light received by the photodetector 124 as described above with respect to the detection signal. Alternatively, the method may comprise supporting the second transparent calibration layer 154 of known refractive index $n_2$ between the calibration surface 114 of the waveguide plate 110 and the second absorptive calibration plate 144 such that an optical interface is formed between the second transparent calibration layer 154 of known refractive index $n_2$ and the calibration surface 114 and performing the steps described above with calibration surface 114 instead of the diagnostic surface 112.

Next, the photodetector 124, the user, the electronics control system 184 (FIG. 5), or another processing unit may determine a relationship between the known refractive index $n_1$, the known refractive index $n_2$, the first calibration detection signal, and the second calibration detection signal. Because the first and second transparent calibration layers 152, 154 comprise known refractive indices $n_1$, $n_2$, respectively, the first and second calibration detection signals determined by the photodetector 124 may be correlated with the refractive indices $n_1$, $n_2$. For example, when the diagnostic light source 120 and the photodetector 124 are Lambertian, the first and second calibration signals may be linearly related to the first and second known refractive indices $n_1$, $n_2$. This linear calibration provides the photodetector 124, the user, the electronics control system 184 (FIG. 5), or another processing unit information regarding the relationship between any detection signal and the critical angle of the emitted light converted by the photodetector 124 into the detection signal. While the calibration method described above comprises a number of steps it should be understood that additional steps may be contemplated. Moreover, while the steps of the calibration method are described in a particular order, other orders are contemplated.

Referring still to FIGS. 2A and 2B, the first and second transparent calibration layers 152, 154 may comprise a flexible polymer material, such as a clear polydimethylsiloxane, a transparent adhesive, a pressure sensitive adhesive such as MyPolymers PS-133®, or the like. For example, when the first transparent calibration layer 152 is supported on the calibration surface 114 and the waveguide plate 110 is oriented such the calibration surface 114 comprises the underside of the waveguide plate 110, for example, as depicted in FIGS. 5A and 5B, the first transparent calibration layer 152 may comprise a transparent adhesive and the first transparent calibration layer 152 may adhesively couple the first absorptive calibration plate 142 to the calibration surface 114. Further, the transparent calibration layers 152, 154 may help limit losses due to evanescent wave coupling that may occur when directly coupling the waveguide plate 110 to a black or opaque material. Moreover, the first transparent calibration layer 152 may be affixed, for example, permanently affixed to the calibration surface 114 of the waveguide plate 110 such that when determining the unknown refractive $n_0$ of an analyte film 150 supported between the light absorption plate 140 and the diagnostic surface 112 of the waveguide plate 110, as described above, the known refractive index $n_1$ of the first transparent calibration layer 152 may comprise the minimum measureable refractive index of the refractometer assembly 100.

The first and second absorptive calibration plates 142, 144 may comprise an opaque glass, an opaque acrylic glass, an opaque plastic, or any other absorptive material. For example, the first and second absorptive calibration plates 142, 144 may comprise black glass, such as black Corning® code 2320 Gorilla® Glass, carbon black-loaded polydimethylsiloxane, or the like. The first and second absorptive calibration plates 142, 144 may comprise the same or different materials. Further, the first and second absorptive calibration plates 142, 144 may comprise the same or different materials as the light absorption plate 140 (FIG. 1). The first and second absorptive calibration plates 142, 144 are each configured to absorb light emitted from the diagnostic light source 120 that reaches the first or second absorptive calibration plates 142, 144 without undergoing internal reflection at the diagnostic surface 112 or the calibration surface 114 of the waveguide plate 110 when the first and/or second transparent calibration layers 152, 154 form optical interfaces with the waveguide plate 110.

Figure 3:
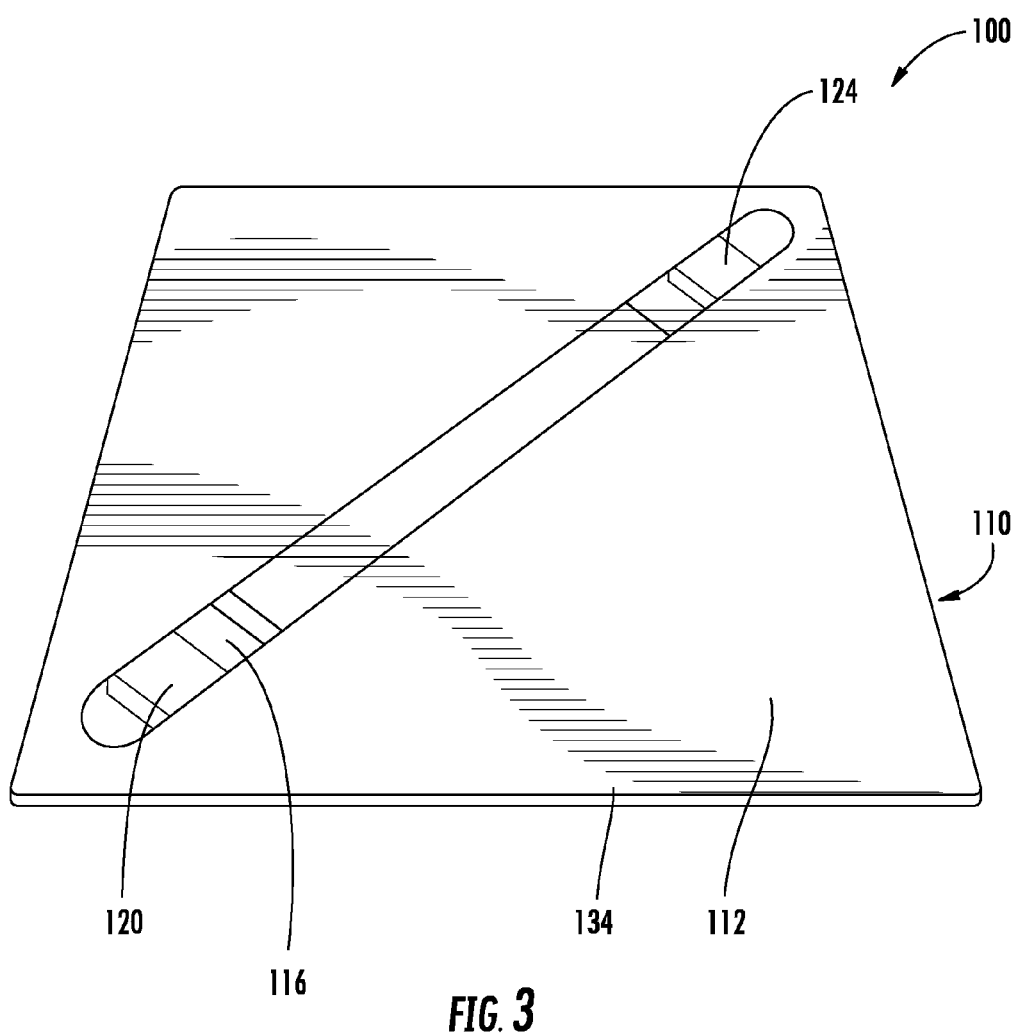
FIG. 3 is a schematic illustration a diagnostic surface of the waveguide plate of FIG. 1, according to one or more embodiments shown and described herein.

Referring now to FIG. 3, the diagnostic surface 112 of the waveguide plate 110 is schematically depicted. A low-friction coating 134 may be positioned on the diagnostic surface 112 of the waveguide plate 110 and may comprise a polymer, a hydrocarbon, a silicone, a fluorosilicone, a fluorocarbon, a self-assembled monolayer (SAM), a fluorosilane coating, an alkylsilane coating, or the like. The low-friction coating 134 may be hydrophobic and/or oleophobic. In operation, the low-friction coating 134 may provide an easy-to-clean coating on the diagnostic surface 112 such that the diagnostic surface 112 may be cleaned before the analyte film 150, the first transparent calibration layer 152, the second transparent calibration layer 154, or other material contacts the diagnostic surface 112. Further, the low-friction coating 134 may comprise the same refractive index as the waveguide plate 110 such that refraction at the optical interface between the analyte film 150 and the diagnostic surface 112 is unaffected by the low-friction coating 134. Alternatively, the low-friction coating 134 may comprise a known refractive index such that any refraction caused by the low-friction coating 134 may be accounted for when determining the unknown refractive index $n_0$ of the analyte film 150. Moreover, the low-friction coating 134 may comprise a thickness of between about 1 nm and about 10 μm, such as about 100 nm, 150 nm, 500 nm, or the like. Refraction of light traversing the low-friction coating 134 comprising a thickness of less than about 1 μm may negligibly effect photodetector 122 measurements such that any refraction caused by the low-friction coating 134 comprising a thickness of less than about 1 μm may not need to be accounted for when determining the unknown refractive index $n_0$ of the analyte film 150.

Figure 4:
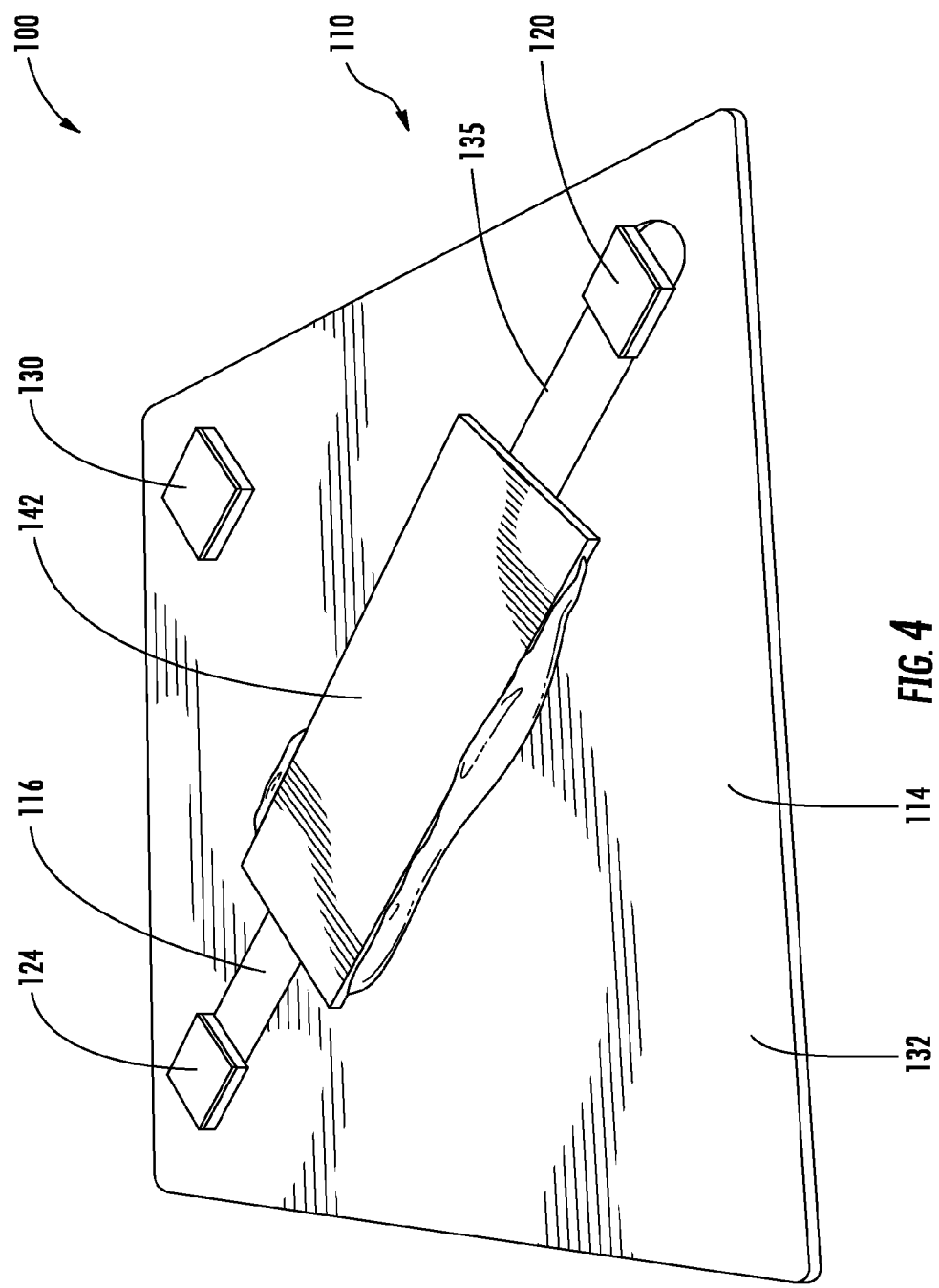
FIG. 4 is a schematic illustration a calibration surface of the waveguide plate of FIG. 1, according to one or more embodiments shown and described herein.

Referring now to FIG. 4, the calibration surface 114 of the waveguide plate 110 is schematically depicted. A peripheral absorption coating 132 may be positioned on a portion of the calibration surface 114. The peripheral absorption coating 132 may comprise any coating compositionally configured to absorb light emitted from the diagnostic light source 120 that reaches the peripheral absorption coating 132. For example, the peripheral absorption coating 132 may comprise an opaque absorptive material, such as a screen printable and/or inkjet printable opaque (e.g., black) ink, an opaque (e.g., black) matrix ink, opaque (e.g., black) paint, adhesive opaque (e.g., black) film, SQS Black—JET7804 ink by SunChemical® SunJet®, or the like. The peripheral absorption coating 132 may be ink-jet printed, screen printed, spin coated, or the like onto the calibration surface 114 of the waveguide plate 110. Further, the peripheral absorption coating 132 may be compositionally configured to absorb light at the emission wavelength of the diagnostic light source 120. Moreover, a portion of the calibration surface 114 on which the peripheral absorption coating 132 is not positioned may comprise a sample testing region 116 that defines an interior perimeter 135 of the peripheral absorption coating 132.

As depicted in FIGS. 3 and 4, the diagnostic light source 120 and the photodetector 124 are each optically coupled to the waveguide plate 110 in optical alignment with the sample testing region 116. For example, the diagnostic light source 120 and the photodetector 124 may each be coupled to the calibration surface 114 or the diagnostic surface 112 within the sample testing region 116. Further, when the analyte film 150 of unknown refractive index $n_0$ forms an optical interface with the diagnostic surface 112 of the waveguide plate 110, the optical interface may be positioned in optical alignment with the sample testing region 116 such that at least a portion of analyte film 150 of unknown refractive index $n_0$ is positioned in contact with the diagnostic surface 112 within the sample testing region 116. Further, the sample testing region 116 may be positioned along the longest linear path of the calibration surface 114, for example, along a diagonal path when the calibration surface 114 is a rectangular shape as depicted in FIGS. 3 and 4.

Referring again to FIG. 4, a temperature sensor 130 may coupled to the waveguide plate 110, for example, coupled to the diagnostic surface 112 and/or the calibration surface 114. The temperature sensor 130 may be structurally configured to measure the temperature of the waveguide plate 110 and/or measure air temperature at the diagnostic surface 112 and/or the calibration surface 114 of the waveguide plate 110. Temperature may alter the refractive index of the waveguide plate 110, the analyte film 150, and the first and second transparent calibration layers 152, 154. Accordingly, temperature measurements may be used when determining the unknown refractive index $n_0$ of the analyte film 150 and when calibrating the refractometer assembly 100. The temperature sensor 130 may comprise a thermistor, a thermocouple, a resistance thermometer, a silicon bandgap temperature sensor, or the like.

Figure 5:
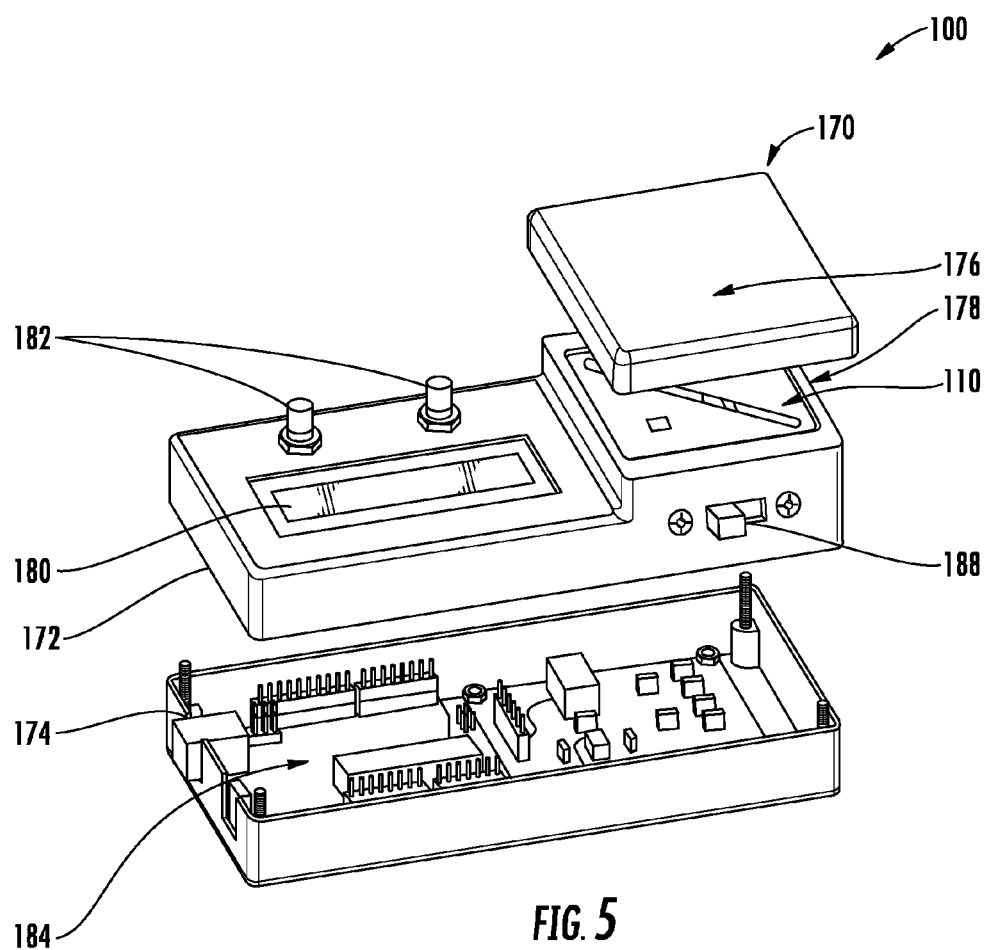
FIG. 5 is a schematic illustration of refractometer assembly having waveguide plate positioned in a waveguide refractometer housing, according to one or more embodiments shown and described herein.

Referring now to FIG. 5, the refractometer assembly 100 may comprise a waveguide plate housing 170 comprising a waveguide plate receiving portion 178 sized and configured to receive the waveguide plate 110. The waveguide plate housing 170 may further comprise a waveguide plate cover 176 engageable with the waveguide plate receiving portion 178 to cover the waveguide plate receiving portion 178. When the waveguide plate 110 is positioned within the waveguide plate receiving portion 178 and the waveguide plate cover 176 is engaged with the waveguide plate receiving portion 178 the waveguide plate cover 176, may prevent light not emitted by the diagnostic light source 120 from entering the waveguide plate 110. For example, waveguide plate cover 176 may be engaged with the waveguide plate receiving portion 178 when determining the unknown refractive index $n_0$ of the analyte film 150 and when calibrating the refractometer assembly 100.

Further, the light absorption plate 140 may be coupled to the waveguide plate cover 176, for example, to an underside of the waveguide plate cover 176 such that when the waveguide plate 110 is positioned within the waveguide plate receiving portion 178, an analyte film 150 is positioned on the diagnostic surface 112 of the waveguide plate 110, and the waveguide plate cover 176 is engaged with the waveguide plate receiving portion 178, the light absorption plate 140 may contact the analyte film 150 such that an optical interface is formed between the diagnostic surface 112 and analyte film 150.

Referring still to FIG. 5, the waveguide plate housing 170 may comprise an upper enclosure 172 removably coupled to a lower enclosure 174, which may each comprise one or more 3D printed materials. As depicted in FIG. 5, the waveguide plate receiving portion 178 may be positioned in the upper enclosure 172, however, it should be understood that the waveguide plate receiving portion 178 may be positioned in the upper enclosure 172 or the lower enclosure 174. Further, it should be understood that the waveguide plate housing 170 may comprise any structural configuration, for example, a unitary housing, or the like.

The waveguide plate housing 170 may further comprise a display 180, one or more user input devices 182 and a power switch 188. The display 180 may include any medium capable of transmitting an optical output such as, for example, a cathode ray tube, light emitting diodes, a liquid crystal display, a plasma display, or the like. Moreover, the display 180 may be a touchscreen that, in addition to providing optical information, detects the presence and location of a tactile input upon a surface of or adjacent to the display. Accordingly, each display 180 may receive mechanical input directly upon the optical output provided by the display 180.

The one or more user input devices 182 are configured to allow the user to communicate with the components of the refractometer assembly 100. The one or more user input devices 182 may be any device capable of transforming user contact into a data signal that can be transmitted such as, for example, a keyboard, buttons, switches, knobs, touch-sensitive pads, microphones, and the like. Further, the one or more user input devices 182 may include a power button (e.g., the power switch 188), a volume button, an activation button, a scroll button, or the like. The one or more user input devices 182 may be used by the user to complete tasks such as programming preferences or settings, providing commands, providing feedback, navigating menus, making selections, and the like.

Referring still to FIG. 5, the waveguide plate housing 170 may further comprise an electronics control system 184 that may be communicatively coupled to one or more of the photodetector 124, the diagnostic light source 120, or the temperature sensor 130, for example, when the waveguide plate 110 is positioned within the waveguide plate receiving portion 178. Further, the electronics control system 184 may be communicatively coupled to the display 180, the one or more user input devices 182, and the power switch 188. As used herein, the term "communicatively coupled" means that coupled components are capable of exchanging data signals with one another such as, for example, electrical signals via conductive medium, electromagnetic signals via air, optical signals via optical waveguides, and the like. The electronics control system 184 may comprise a processing unit, for example, an Arduino® microcontroller, such as the Arduino® UNO® microcontroller or a PIC® microcontroller. However, it should be understood that any processing unit, such as microcontrollers, electronics controllers, processors, or the like are contemplated. Further, the electronics control system 184 may comprise one or more memory modules communicatively coupled to the processing unit.

In operation, the electronics control system 184 may provide control signals to the diagnostic light source 120 and may receive detection signals from the photodetector 124 and may be programmed to determine the refractive index $n_0$ of the analyte film 150 based on the detection signals received from the photodetector 124. Further, the electronics control system 184 may provide control signals to the display 180, for example, to display the detection signal and the determined refractive index. Moreover, the electronics control system 184 may provide and receive control signals from the one or more user input devices 182 and the power switch 188.

The electronics control system 184 may further comprise one or more operational amplifiers (op-amps), a DC-DC converter, for example, a DB02S4815A-DCDC converter, and an input digital voltage sensor. For example, in operation, the DC-DC converter may provide a positive and negative voltage rail for the one or more op-amps and the input digital voltage sensor may comprise a voltage operating range, for example, between about 0 Volts (V) and about 5 V. The one or more op-amps positive input supply rail and negative input supply rail may be biased outside of the voltage operating range, for example, to achieve the maximum digital input range (e.g., detection signal range) of the electronics control system 184. Moreover, the electronics control system 184 may be configured such that the DC-DC converter and the op-amps are powered on when the diagnostic light source 120 and photodetector 124 are operating and powered off when the diagnostic light source 120 and photodetector 124 are not operating. The electronics control system 184 may further comprise a transimpedance amplifier (TIA) configured to convert current to voltage, for example, when the processor and/or microcontroller of the electronics control system 184 are configured to detect voltage levels. For example, when the detecting portion of the photodetector 124 comprises a photodiode, the current response of the photodiode to received light may be more linear that the voltage response of the photodiode to received light. It should be understood that the electronics control system 184 is not limited to the specific components described above and may comprise any electronics control system and corresponding components structurally configured to perform the functions described herein.

Further, the display 180, the one or more user input devices 182, the electronics control system 184, and/or the power switch 188 may be located in a device separate from the waveguide plate 110 and the waveguide plate housing 170, for example a smart phone, a tablet, e-reader, or the like. The separate device may be communicatively coupled to the diagnostic light source 120, the photodetector 124, the temperature sensor 130 using a wired connection, for example, a cable connection, an audio jack connection, or the like, or using a wireless connection, for example, RF, WiFi, Bluetooth®, Bluetooth® LE, or the like. Moreover, operation of the refractometer assembly 100 may be implemented by a computer program product such as a mobile device application, which may stored in the one or more memory modules of the electronics control system 184.

It is noted that recitations herein of a component of the present disclosure being "configured" in a particular way, to embody a particular property, or to function in a particular manner, are structural recitations, as opposed to recitations of intended use. More specifically, the references herein to the manner in which a component is "configured" denotes an existing physical condition of the component and, as such, is to be taken as a definite recitation of the structural characteristics of the component.

For the purposes of describing and defining the present invention it is noted that the term "about" is utilized herein to represent the inherent degree of uncertainty that may be attributed to any quantitative comparison, value, measurement, or other representation. The term "about" is also utilized herein to represent the degree by which a quantitative representation may vary from a stated reference without resulting in a change in the basic function of the subject matter at issue.

Having described the subject matter of the present disclosure in detail and by reference to specific embodiments thereof, it is noted that the various details disclosed herein should not be taken to imply that these details relate to elements that are essential components of the various embodiments described herein, even in cases where a particular element is illustrated in each of the drawings that accompany the present description. Further, it will be apparent that modifications and variations are possible without departing from the scope of the present disclosure, including, but not limited to, embodiments defined in the appended claims. More specifically, although some aspects of the present disclosure are identified herein as preferred or particularly advantageous, it is contemplated that the present disclosure is not necessarily limited to these aspects.

It is noted that one or more of the following claims utilize the term "wherein" as a transitional phrase. For the purposes of defining the present invention, it is noted that this term is introduced in the claims as an open-ended transitional phrase that is used to introduce a recitation of a series of characteristics of the structure and should be interpreted in like manner as the more commonly used open-ended preamble term "comprising."

What is claimed is:

1. A refractometer assembly comprising a waveguide plate, a diagnostic light source, a photodetector, and a light absorption plate, wherein:
    the waveguide plate comprises a diagnostic surface configured to support an analyte film of unknown refractive index $n_0$ between the light absorption plate and the diagnostic surface of the waveguide plate;
    the diagnostic light source is characterized by an emission profile that is approximately Lambertian;
    the diagnostic light source and the photodetector are optically coupled to the waveguide plate such that at least a portion of the light emitted from the diagnostic light source is subject to internal reflection at the diagnostic surface of the waveguide plate prior to reaching the photodetector when the analyte film of unknown refractive index $n_0$ forms an optical interface with the diagnostic surface of the waveguide plate;
    the light absorption plate is configured to absorb light emitted from the diagnostic light source and reaching the light absorption plate without undergoing internal reflection at the diagnostic surface of the waveguide plate when the analyte film of unknown refractive index $n_0$ forms an optical interface with the diagnostic surface of the waveguide plate;
    the waveguide plate, the diagnostic light source, the photodetector, and the light absorption plate collectively define an optical system where variations in the unknown refractive index $n_0$ are related to variations in a detection signal generated by the photodetector.

2. The refractometer assembly of claim 1, wherein the diagnostic light source comprises a light emitting portion and a Lambertian scattering layer optically coupling the light emitting portion to the waveguide plate.

3. The refractometer assembly of claim 2, wherein the Lambertian scattering layer is positioned between and adhesively couples the light emitting portion to the diagnostic surface of the waveguide plate.

4. The refractometer assembly of claim 2, wherein the Lambertian scattering layer is positioned between and adhesively couples the light emitting portion to a calibration surface of the waveguide plate opposite the diagnostic surface of the waveguide plate.

5. The refractometer assembly of claim 1, wherein the diagnostic light source is characterized by an emission profile that is approximately Lambertian over a solid angle that is at least large enough to span a range over which total internal reflection of diagnostic light within the waveguide plate is supported.

6. The refractometer assembly of claim 1, wherein the photodetector comprises a detecting portion and a Lambertian cosine correcting layer optically coupling the detecting portion to the waveguide plate.

7. The refractometer assembly of claim 6, wherein the Lambertian cosine correcting layer is positioned between and adhesively couples the detecting portion to one of the diagnostic surface or a calibration surface opposite the diagnostic surface.

8. The refractometer assembly of claim 1, wherein the variations in the unknown refractive index $n_0$ are linearly related to the variations in the detection signal generated by the photodetector.

9. The refractometer assembly of claim 1, wherein:
    the waveguide plate comprises a peripheral absorption coating positioned on a calibration surface that is opposite the diagnostic surface;
    the peripheral absorption coating is structurally configured to absorb light emitted from the diagnostic light source that reaches the peripheral absorption coating; and
    an interior perimeter of the peripheral absorption coating defines a sample testing region of the calibration surface.

10. The refractometer assembly of claim 9, wherein:
    the diagnostic light source and the photodetector are each optically coupled to the waveguide plate in optical alignment with the sample testing region; and
    when the analyte film of unknown refractive index $n_0$ forms an optical interface with the diagnostic surface of the waveguide plate, the optical interface is positioned in optical alignment with the sample testing region.

11. The refractometer assembly of claim 1, further comprising low-friction coating positioned on the diagnostic surface of the waveguide plate.

12. The refractometer assembly of claim 1, further comprising a first absorptive calibration plate configured to absorb light emitted from the diagnostic light source and reaching the first absorptive calibration plate without undergoing internal reflection at one of the diagnostic surface or a calibration surface opposite the diagnostic surface when a first transparent calibration layer of known refractive index $n_1$ forms an optical interface with one of the diagnostic surface or the calibration surface.

13. The refractometer assembly of claim 12, further comprising a second absorptive calibration plate configured to absorb light emitted from the diagnostic light source and reaching the second absorptive calibration plate without undergoing internal reflection at one of the diagnostic surface or the calibration surface when a second transparent calibration layer of known refractive index $n_2$ forms an optical interface with one of the diagnostic surface or the calibration surface.

14. The refractometer assembly of claim 13, wherein the first absorptive calibration plate and the second absorptive calibration plate each comprise an opaque glass plate.

15. The refractometer assembly of claim 1, wherein the waveguide plate comprises a glass plate.

16. The refractometer assembly of claim 1, further comprising a waveguide plate housing comprising a waveguide plate receiving portion and a waveguide plate cover engageable with the waveguide plate receiving portion.

17. A method of determining an unknown refractive index $n_0$ of an analyte film, the method comprising:
    emitting light from a diagnostic light source optically coupled to a waveguide plate wherein:

an analyte film of unknown refractive index $n_0$ is supported between a light absorption plate and a diagnostic surface of the waveguide plate such that the analyte film of unknown refractive index $n_0$ forms an optical interface with the diagnostic surface of the waveguide plate;

the emitted light is characterized by an emission profile that is approximately Lambertian; and the light absorption plate is configured to absorb light emitted from the diagnostic light source and reaching the light absorption plate without undergoing internal reflection at the diagnostic surface of the waveguide plate when the analyte film of unknown refractive index $n_0$ forms an optical interface with the diagnostic surface of the waveguide plate;

converting a portion of emitted light that is subject to internal reflection at the diagnostic surface of the waveguide plate into a detection signal using a photodetector optically coupled to the waveguide plate wherein the unknown refractive index $n_0$ is related to the detection signal; and determining the unknown refractive index $n_0$ based on the detection signal.

18. A method of calibrating a refractometer assembly comprising a waveguide plate, a diagnostic light source, and a photodetector, the method comprising:

supporting a first transparent calibration layer of known refractive index $n_1$ between a calibration surface of the waveguide plate and a first absorptive calibration plate such that an optical interface is formed between the first transparent calibration layer of known refractive index $n_1$ and the calibration surface;

emitting light from the diagnostic light source optically coupled to the waveguide plate, wherein:
 the emitted light is characterized by an emission profile that is approximately Lambertian; and
 the first absorptive calibration plate is configured to absorb light emitted from the diagnostic light source and reaching the first absorptive calibration plate without undergoing internal reflection at the calibration surface of the waveguide plate when first transparent calibration layer of known refractive index $n_1$ forms an optical interface with the calibration surface of the waveguide plate;

converting a portion of emitted light that is subject to internal reflection at the calibration surface of the waveguide plate into a first calibration detection signal using the photodetector optically coupled to the waveguide plate;

supporting a second transparent calibration layer of known refractive index $n_2$ between a diagnostic surface of the waveguide plate and a second absorptive calibration plate such that an optical interface is formed between the second transparent calibration layer of known refractive index $n_2$ and the diagnostic surface, wherein the diagnostic surface is opposite the calibration surface;

emitting light from the diagnostic light source optically coupled to the waveguide plate, wherein:
 the emitted light is characterized by an emission profile that is approximately Lambertian; and
 the second absorptive calibration plate is configured to absorb light emitted from the diagnostic light source and reaching the second absorptive calibration plate without undergoing internal reflection at the diagnostic surface of the waveguide plate when the second transparent calibration layer of known refractive index $n_2$ forms an optical interface with the diagnostic surface of the waveguide plate;

converting a portion of emitted light that is subject to internal reflection at the diagnostic surface of the waveguide plate into a second calibration detection signal using the photodetector optically coupled to the waveguide plate; and determining a relationship between the known refractive index $n_1$, the known refractive index $n_2$, the first calibration detection signal, and the second calibration detection signal.

19. The method of claim 18, wherein the first transparent calibration layer comprises a transparent adhesive.

20. The method of claim 18, wherein the first absorptive calibration plate and the second absorptive calibration plate each comprise an opaque glass plate.

* * * * *

UNITED STATES PATENT AND TRADEMARK OFFICE
CERTIFICATE OF CORRECTION

PATENT NO. : 10,078,048 B2  
APPLICATION NO. : 15/415283  
DATED : September 18, 2018  
INVENTOR(S) : Colin Brendan Daly et al.

Page 1 of 1

It is certified that error appears in the above-identified patent and that said Letters Patent is hereby corrected as shown below:

In the Specification

In Column 1, Line 14, after "entirety" insert -- . --.

Signed and Sealed this
Twelfth Day of January, 2021

Andrei Iancu
*Director of the United States Patent and Trademark Office*